(12) United States Patent
Russell

(10) Patent No.: US 7,077,137 B2
(45) Date of Patent: Jul. 18, 2006

(54) BREATHING DEVICE FOR FILTERING AND CONDITIONING INHALED AIR

(76) Inventor: James K. Russell, 3948 Gondar Ave., Long Beach, CA (US) 90809

( * ) Notice: Subject to any disclaimer, the term of this patent is extended or adjusted under 35 U.S.C. 154(b) by 309 days.

(21) Appl. No.: 10/453,722

(22) Filed: Jun. 2, 2003

(65) Prior Publication Data

US 2004/0237962 A1    Dec. 2, 2004

(51) Int. Cl.
 *A62B 18/08* (2006.01)
 *A41H 1/04* (2006.01)
 *A61F 9/02* (2006.01)

(52) U.S. Cl. .......................... 128/206.12; 128/201.12; 2/6.7; 2/428

(58) Field of Classification Search ........... 128/200.27, 128/200.28, 201.12, 201.14, 201.15, 201.17, 128/201.23, 201.24, 201.25, 205.25, 205.29, 128/206.12, 206.13, 206.16, 206.19, 206.21, 128/206.23, 206.28, 207.11, 207.13; 2/6.7, 2/1, 8, 9, 424, 426–429, 436
See application file for complete search history.

(56) References Cited

U.S. PATENT DOCUMENTS

| | | | |
|---|---|---|---|
| 3,991,753 A * | 11/1976 | Viesca y Viesca | ..... 128/201.12 |
| 4,944,039 A * | 7/1990 | Dietrich | ............................ 2/13 |
| 5,438,710 A | 8/1995 | McDonald | |
| 5,697,100 A | 12/1997 | Horowitz | |
| 5,704,063 A * | 1/1998 | Tilden | ................................ 2/9 |
| 5,956,119 A * | 9/1999 | Gibbs | ........................ 351/158 |
| 6,532,598 B1 | 3/2003 | Cardarelli | |

* cited by examiner

*Primary Examiner*—Henry Bennett
*Assistant Examiner*—Teena Mitchell
(74) *Attorney, Agent, or Firm*—Orrick, Herrington & Sutcliffe, LLP

(57) ABSTRACT

A personal breathing device for filtering, diffusing, and conditioning air inhaled by a person. The device includes an eyewear frame with an attached nose piece and air-permeable membrane which is positioned to surround the nose and permit normally inhaled volumes of air to pass through the membrane as the air is inhaled, and thereby filter and condition the inhaled air. The device can be conveniently placed on and removed from the face, does not obstruct speech, and is suitable for wearing during a variety of normal daily activities to filter and condition inhaled air. The air permeable membrane can be impregnated with various liquids or other agents to enhance filtering and antimicrobial functions, or to provide cooling, moisturizing, or scenting of the inhaled air. The device can be provided with a detachable air permeable membrane which can be easily replaced as needed.

17 Claims, 2 Drawing Sheets

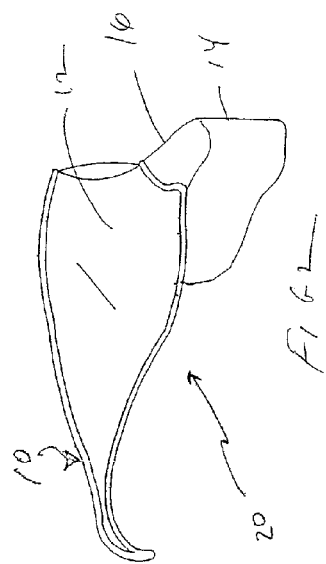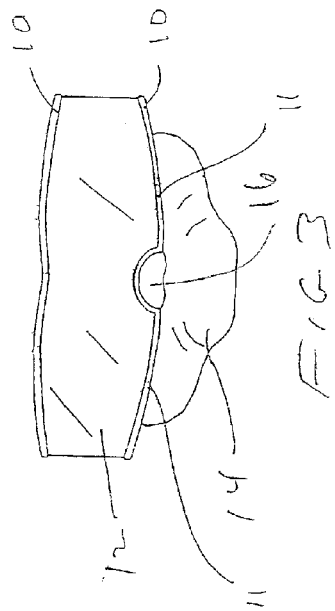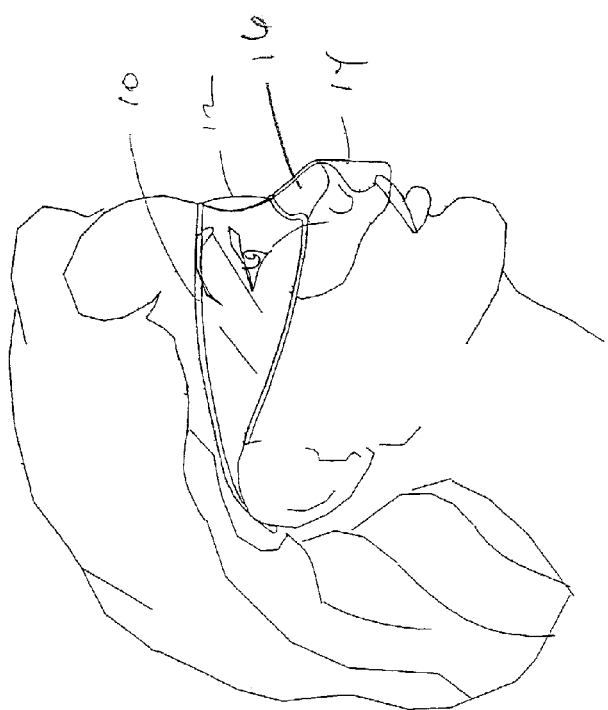

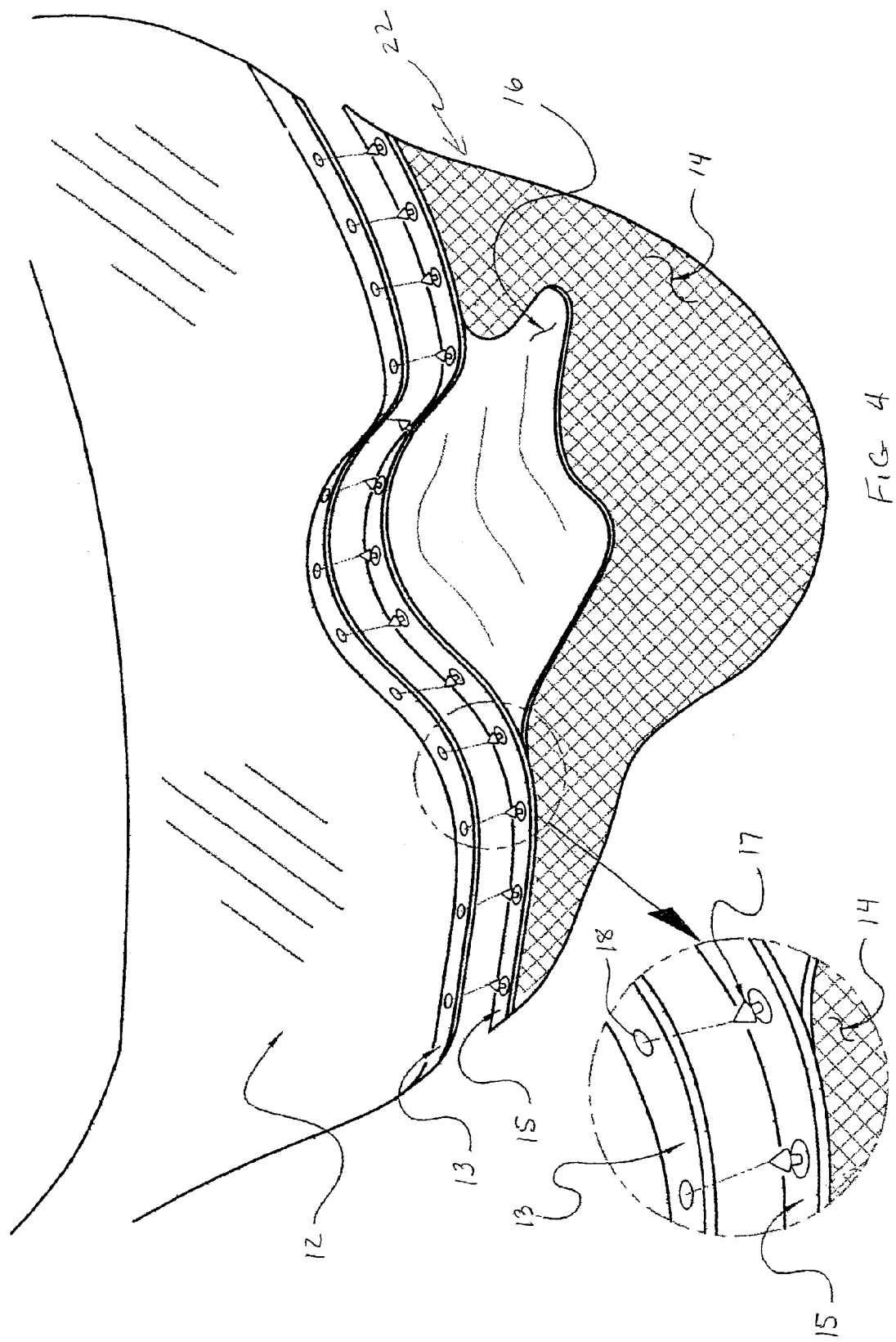

BREATHING DEVICE FOR FILTERING AND CONDITIONING INHALED AIR

The present invention relates to a personal breathing device, and more particularly to an air filtering device which includes a filter membrane for filtering and conditioning a person's inhaled air, which can be conveniently placed on and removed from the person's face, and which is suitable for wearing during a variety of normal daily activities.

BACKGROUND OF THE INVENTION

Protective personal respiratory masks of various types have long been used to cover the wearer's nose and mouth and filter the air breathed by the wearer. Well known examples of such masks are surgical masks used by medical personnel and others to reduce spread of microorganisms, and dust masks used by workers to reduce inhalation of dust and other airborne particulates. Such breathing masks are made of a variety of air-permeable materials, including one or more layers of woven or non-woven fabrics and materials, and are generally disposed of after a single use. Such masks may be molded into a domed shape which fits on the wearer's face over the nose and mouth, and is secured around the wearer's head by an elastic band. An example of a molded disposable breathing mask is the Model N95 particulate respirator and surgical mask sold by 3M Company. Other such molded masks are generally available at hardware stores and other retail outlets. Another type of protective breathing mask is a typical surgical mask which comprises a rectangle of layered material having parallel flat folds with a string tie or ear loop attached to each corner, and which is placed over the nose and mouth and secured by the ties or ear loops to the wearer's head or ears.

These protective respiratory masks are most frequently worn by individuals in a work setting, such as in a hospital or other healthcare facility to reduce the transmission of airborne microorganisms to or from the wearer. Such masks are also used to protect individuals working in construction or manufacturing settings where they are exposed to air which is filled with dust or other particulates. Individuals may also use such masks in non-work settings to reduce inhalation of dust while performing, e.g., yard work or house cleaning, or to reduce exposure to pollen or other airborne particulates or microorganisms.

Increasingly, individuals in today's health-conscious and active society desire to wear a personal protective respiratory mask when going about daily activities to reduce their exposure to airborne contaminants in public places or during recreational activities. Such contaminants may include smog, dust, pollen, germs, and other particulates, or offensive odors. As one example, the recent worldwide SARS (Severe Acute Respiratory Syndrome) epidemic has resulted in an increase in the number of people who wish to wear a personal respiratory mask while traveling in public places to reduce their exposure risks. In fact, the World Health Organization has recommended that individuals wear personal protective respiratory masks to help stop the spread of the disease.

However, the existing personal protective inhalation masks currently available have a number of drawbacks, including that they are cumbersome and unattractive, they make communication more difficult because they cover the mouth, they partially obstruct the view of the wearer, and may be uncomfortable to wear due to their method of attachment to the head. Further, they are inconvenient because they do not lend themselves to being readily put on and taken off, and are better suited for use in a work setting, rather than for use during everyday and casual activities.

Therefore, there is a need for a personal protective respiratory mask that can be conveniently worn by individuals while going about daily activities and will provide air filtration and freshening of one's ambient air before it is inhaled.

SUMMARY OF THE INVENTION

The present invention is a novel personal breathing device which is wearable by an individual for filtering and conditioning the person's breathable air just before the air is inhaled, and is no more cumbersome to wear and use than a pair of sunglasses. The apparatus is designed to be conveniently worn or removed as desired while going about one's normal daily activities, and to condition the inhaled air by filtration, freshening, hydrating, and/or cooling at least a portion of the air being inhaled by the person. The apparatus includes a fitted but loosely worn filter or diffuser membrane which is attached to an eyewear frame at a position to allow one's normally inhaled volumes of air to pass over, under, around and through the membrane prior to inhalation to provide at least partial filtering and conditioning of the air and removal of airborne contaminants.

The surfaces of the air permeable membrane condition the inhaled air as it passes through the membrane by reducing the amount of airborne particles, microorganisms, and other contaminants in the inhaled air, such as ambient odors, pollens, impurities, dust, fungi, bacteria, viruses, and other respiratory pathogens and transient microorganisms. The membrane may be impregnated with various agents and/or wetted with various liquids to enhance the capability of the membrane to trap contaminants, or to provide cooling, moisturizing, or scenting of the inhaled air. The device thereby permits the wearer to conduct daily activities while providing a convenient and desirable means to obtain an improved quality of inhaled air.

In an exemplary embodiment, the apparatus comprises an eyewear frame and lens assembly easily wearable by an individual, and having an attached microporous membrane to condition and thereby modify the air passing therethrough into the wearer's nose and/or mouth. The eyewear assembly may be of a wraparound design through which the observer can see, and the membrane is attached to the eyewear assembly so as not to obstruct the vision of the wearer. The attached filter membrane is preferably a microporous membrane which is smooth and non-irritating and which can optionally be wetted and/or impregnated with, for example, water and other liquids, emollients, anti-bacterial components and the like. The device's design as an eyewear assembly facilitates putting the device on when needed and taking it off when not needed.

Accordingly, it is an object of the present invention to provide an improved wearable device for conditioning an individual's breathable air. Another object of the present invention is to provide a eyewear frame and lens assembly to fit over an individual's eyes and nose and which further includes a suitable air permeable material for conditioning the individual's breathable air.

These and other objects and features of the present invention will become better understood through a consideration of the following drawings in which:

BRIEF DESCRIPTION OF THE DRAWINGS

FIG. 1 is a side elevational view of an individual wearing a device according to the present invention, FIG. 2 is a side elevational view of the device, FIG. 3 is a front elevational view of the device; and FIG. 4 is a front view of an embodiment of the device having separate but attachable eyewear and air filtration member components.

FIG. 4a is an enlarged version of a portion of FIG. 4 showing the details of a barbed connector attachment.

DETAILED DESCRIPTION

Turning now to the drawings, an exemplary embodiment of a personal breathing device 20 for filtering, diffusing, and conditioning inhaled air according to the present invention is shown in FIGS. 1–3. The device 20 includes a frame 10 configured to fit around the forehead and upper portion of the nose of an individual and extending back to the vicinity behind the ears for retaining the device on the head of the wearer. Preferably the frame is formed of lightweight material, such as plastic or a lightweight metal. A suitable lens 12 is affixed within the frame 10, and is formed of any material having suitable transparent optical properties, including clear and colored plastics suitable for use in, e.g., protective eyewear such as sunglasses or safety glasses.

The device includes a forward section or support member 16 attached to and extending outward from the center of the lower portion 11 of the eyewear frame, and an air-permeable membrane 14 attached to the eyewear frame and partially supported by support member 16. Support member 16 may be made of a smooth plastic or other material to have a shape such as, e.g., the nosepiece shown in FIGS. 1–4 which will extend over and around the top of the lower and tip portion of a person's nose when the device 20 is worn by the person. As shown in FIG. 1, the air permeable membrane 14 surrounds the nose and area adjacent the nose and extends downward preferably to at least the upper lip of the wearer, as best seen in FIG. 1.

The air permeable membrane 14 comprises a stable, soft, lightweight, non-abrasive woven or non-woven air permeable material. As shown in FIG. 1, membrane 14 is attached to the lower portion 11 of the eyewear frame 10, and is positioned in relation to the support member 16 so that the membrane does not obstruct the wearer's breathing path and permits high air flow rates.

The membrane 14 preferably has a high filtration efficiency, and most preferably greater than 95% 0.1 micron filter efficiency. The membrane 14 also preferably has high thermal endurance, high resistance to chemical attack, and a low coefficient of expansion. Where it is desired to utilize a wetted membrane, the membrane 14 can be selected to minimize moisture loss. A wetted membrane may be utilized to add moisture to inhaled air and/or to enhance removal of particulates from the inhaled air. One example of a suitable membrane material is the Magna(™) Nylon membrane sold by Osmonics, Inc. (Minnetonka, Minn.), which is an engineered naturally hydrophilic filtration membrane having an internal polyester support web to give it dimensional strength and stability, and is designed to wet out evenly. The membrane 14 may be optionally saturated with a variety of non-toxic, non-allergenic, high quality, additives, including fragrances, anti-microbial agents, emollients, or wetting agents including, e.g., solutions which will not evaporate quickly and will lubricate and soften minor skin and membranes irritations, deter dryness, aid rehydration, increase recovery of sensitive organisms, contribute to anti-viral intervention and therapy, and suppress the growth of negative bacteria, fungi and viral respiratory pathogens. If desired, a fluid reservoir (not shown) may be provided attached to the eyewear frame with a wick attachable to the air permeable membrane 14 to maintain the membrane in a wetted condition while worn.

The air permeable membrane 14 may be permanently or releasably attached to the lower portion 11 of the eyewear frame by any suitable attachment arrangement. As will be readily discerned by those skilled in the art, suitable attachments may include, but are not limited to, e.g., adhesives, barbed precision plastic tubing connectors, interconnecting plastic pairs, low profile pressure sensitive closure systems (e.g., Velcro), self-locking/self-engaging fasteners with molded plastic resin fasteners backed with rubber, molded tape with pressure sensitive release film backing, soft fasteners made of woven fastening tapes or polyester fasteners, and the like.

As shown in FIG. 4, the air permeable membrane 14 and support member 16 may be provided as a separate air filtration member 22 for attachment to the eyewear frame 10. Such a separate air filtration member may be provided with a releasable attachment so that the air filtration member 22 may be subsequently removed and replaced with a new air filtration member 22 as needed. Alternately, support member 16 may remain attached to the eyewear frame, and only the air permeable membrane 14 may be releaseably attached to the eyewear frame.

An exemplary attachment arrangement is shown in FIGS. 4 and 4a, in which minute barbed precision plastic male and female connectors 17 and 18, respectively, provide the attachment function. The female connectors 18 may be molded into a lower surface of the eyewear frame, or into a first attachment strip 13 attached to the lower surface of the eyewear frame. The male connectors 17 may be part of a second attachment strip 15 which is attached to the air permeable membrane 14, or may be adhesion or fusion bonded directly to the air permeable membrane 14. The second attachment strip 15 may carry upon it a low profile, pressure sensitive adhesive to assist in the attachment and adhesion to the eyewear frame.

Support member 16 may be any suitable size and shape to direct membrane 14 out and over the wearer's nose, and may be made of any suitable material such as plastic, wire mesh, heavy weight membrane material, and the like. Support member 16 may be adhesion or fusion bonded to the second attachment strip, or it may be bonded to the filter membrane 14. Support member 16 may alternately be a shaped or stiffened portion of the membrane itself. Support member 16 may be perforated or otherwise made air permeable to facilitate passage of air through the adjacent membrane.

In another embodiment of the personal breathing device of this invention (not shown), the air permeable membrane 14 and support member 16 are attached to a modified eyewear frame having only a lower frame portion extending from the wearer's ears and across the bridge of the nose below the eyes, without any lens portion. If desired, the frame may be made of a flexible material which may be shaped by the wearer to conform to the contours of the person's face and nose.

While embodiments of the present invention have been shown and described, various modifications may be made without departing from the scope of the present invention, and all such modifications and equivalents are intended to be covered.

What is claimed is:

1. A device wearable by a person for conditioning inhaled air, comprising:
    an eyewear frame shaped to extend from the vicinity behind the ears of a person and over the eye area of the person's face, the frame including an upper portion for extending across the person's forehead above the eyes and a lower portion for extending across the bridge of the person's nose below the eyes,
    a transparent lens disposed in the frame for allowing visibility for the person wearing the device, and
    an air filtration member attached to the lower portion of the eyewear frame, wherein the filtration member comprises a support member shaped and positioned to extend outward from the frame over the tip of the person's nose and an air-permeable membrane extending generally downward from the eyewear frame, said membrane being of sufficient length and size to extend below the person's nose and to cover at least a portion of the person's mouth and face, and being directed out from and over the person's nose by said support member.

2. The device of claim 1 further comprising an attachment for releasably attaching the air-permeable membrane to the lower portion of the eyewear frame.

3. The device of claim 2 wherein said membrane is moistened with water or a water-containing fluid.

4. The device of claim 2 wherein said membrane contains an anti-microbial agent.

5. The device of claim 2 wherein said membrane contains a moisturizing agent.

6. The device of claim 2 wherein said membrane contains a fragrance.

7. A device wearable by a person for conditioning inhaled air, comprising:
    an eyewear frame shaped to extend from the vicinity behind the ears of a person and over the eye area of the person's face, the frame including an upper portion for extending across the person's forehead above the eyes and a lower portion for extending across the bridge of the person's nose below the eyes,
    a transparent lens disposed in the frame for allowing visibility for the person wearing the device, and
    an air filtration member comprising connectors for releasably attaching said member to the lower portion of the eyewear frame, a support member shaped and positioned to extend outward from the frame over the tip of the person's nose, and an air-permeable membrane extending generally downward from the eyewear frame, said membrane being of sufficient length and size to extend below the person's nose and to cover at least a portion of the person's mouth and face, and being directed out from and over the person's nose by said support member.

8. The device of claim 7 wherein said connectors comprise barbed male connectors.

9. The device of claim 8 wherein the lower portion of the eyewear frame contains female connectors shaped to receive said barbed male connectors.

10. A device for placement on a person's face for conditioning inhaled air, comprising:
    a support frame shaped to generally extend from the vicinity behind the ears of a person and across the bridge of the person's nose below the eyes,
    a membrane support member attached to the support frame positioned and shaped to extend outward over the tip of the person's nose when the support frame is positioned on the person's face, and
    an air-permeable membrane attached to the support frame such that the membrane extends generally downward from the support frame, and is directed out from and over the person's nose by the membrane support member, said membrane being of sufficient length and size to extend below the person's nose and to cover at least a portion of the person's mouth and face.

11. A device for placement on a person's face for conditioning inhaled air, comprising:
    a support frame shaped to generally extend from the vicinity behind the ears of a person and across the bridge of the person's nose below the eyes,
    a membrane support member attached to the support frame positioned and shaped to extend outward over the tip of the person's nose when the support frame is positioned on the person's face, and
    an air-permeable membrane attached over the support frame such that the membrane extends generally downward from the support frame, and is directed out from and over the person's nose by the membrane support member, said membrane being of sufficient length and size to extend below the person's nose and to cover at least a portion of the person's mouth and face, and said membrane having high filtration efficiency.

12. A device as in claim 11 wherein the membrane is a hydrophilic filtration membrane.

13. A device wearable by a person for conditioning inhaled air, comprising:
    an eyewear frame shaped to extend from the vicinity behind the ears of a person and over the eye area of the person's face, the frame including an upper portion extending across the person's forehead above the eyes and a lower portion extending across the bridge of the person's nose below the eyes,
    a lens disposed in the frame for allowing visibility for the person wearing the device, and
    an air filtration member comprising a hydrophilic filtration membrane attached to the lower portion of the eyewear frame, wherein the filtration member includes a support shaped and positioned to extend outward from the frame over the tip of the person's nose and an air-permeable membrane extending generally downward from the eyewear frame, said membrane being of sufficient length and size to extend below the person's nose and to cover at least a portion of the person's mouth and face, and being directed out from and over the person's nose by said support member.

14. The device of claim 13 wherein said membrane is adapted to be moistened with water or a water-containing fluid.

15. The device of claim 13 wherein said membrane contains an anti-microbial agent.

16. The device of claim 13 wherein said membrane contains a moisturizing agent.

17. The device of claim 13 wherein said membrane contains a fragrance.

* * * * *